United States Patent
Lia et al.

(10) Patent No.: US 9,814,377 B2
(45) Date of Patent: Nov. 14, 2017

(54) MEDICAL INSTRUMENT HAVING LED ILLUMINATION SYSTEM

(71) Applicant: Welch Allyn, Inc., Skaneateles Falls, NY (US)

(72) Inventors: Raymond A. Lia, Auburn, NY (US); Robert L. Vivenzio, Auburn, NY (US); John R. Strom, Moravia, NY (US); Ervin Goldfain, Syracuse, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 42 days.

(21) Appl. No.: 14/957,813

(22) Filed: Dec. 3, 2015

(65) Prior Publication Data

US 2017/0156578 A1 Jun. 8, 2017

(51) Int. Cl.
| | |
|---|---|
| *A61B 1/06* | (2006.01) |
| *A61B 90/30* | (2016.01) |
| *A61B 1/227* | (2006.01) |
| *A61B 1/00* | (2006.01) |

(52) U.S. Cl.
CPC ........ *A61B 1/0684* (2013.01); *A61B 1/00163* (2013.01); *A61B 1/227* (2013.01); *A61B 90/30* (2016.02); *A61B 2090/304* (2016.02)

(58) Field of Classification Search
CPC ... A61B 1/0684; A61B 1/00163; A61B 1/227; A61B 90/30; A61B 2090/304
USPC .................................................. 600/199, 200
See application file for complete search history.

(56) References Cited

U.S. PATENT DOCUMENTS

| | | | |
|---|---|---|---|
| 3,728,998 A | 4/1973 | Heine | |
| 4,006,738 A | 2/1977 | Moore et al. | |
| 2003/0187331 A1* | 10/2003 | Faludi | A61B 1/0607 600/200 |
| 2013/0120980 A1* | 5/2013 | Eichenholz | F21V 13/14 362/231 |
| 2014/0073858 A1* | 3/2014 | Sherwinter | A61B 17/1114 600/249 |
| 2015/0351637 A1* | 12/2015 | Ruppersberg | A61B 1/00179 600/474 |

\* cited by examiner

*Primary Examiner* — Pedro Philogene
*Assistant Examiner* — David C Comstock
(74) *Attorney, Agent, or Firm* — Barclay Damon, LLP

(57) ABSTRACT

A medical diagnostic instrument includes a housing having an interior, a distal end and an opposing proximal end. A supporting member is disposed within the interior of the housing, and supports a plurality of LEDs. A light guide made from a light transmissive material is distally disposed in relation to the LED supporting member for transmitting light emitted by the plurality of LEDs through the distal end of the housing. In at least one version, at least one end of the light guide can be provided with a patterned surface that is configured to produce a uniform illumination spot.

17 Claims, 10 Drawing Sheets

MEDICAL INSTRUMENT HAVING LED ILLUMINATION SYSTEM

TECHNICAL FIELD

This application generally relates to the field of diagnostic medicine and more specifically to a medical diagnostic instrument, such as an otoscope, having an LED-based illumination system that effectively and uniformly disperses emitted light to an intended target of interest.

BACKGROUND

Several medical diagnostic instruments are commonly used by physicians, clinicians, and other caregivers for conducting various facets of a patient examination; for example, a typical wellness visit. These diagnostic instruments are typically directed to specific medical targets; for example, otoscopes are used for examining the ear, ophthalmoscopes are used for examining the eye, rhinoscopes are used for examining the nose, and larygnoscopes are used for examining the throat, among others. Typical versions of these instruments, such as those manufactured and sold by Welch Allyn, Inc. of Skaneateles Falls, N.Y., are designed to be held within a single hand of a caregiver. More specifically, each instrument typically is defined by a compact housing that retains an illumination system configured for adequately visualizing the intended target, either using the eye of the caregiver or electronically in which an image of the target is focused by a contained optical assembly onto an imager.

Early versions of the above-noted instruments, such as described in U.S. Pat. Nos. 3,728,998 and 4,006,738, employ incandescent or halogen bulbs as light sources. While providing adequate illumination of the intended medical target for viewing purposes, light bulbs generate high amounts of heat and power consumption and also have a relatively short working life.

In order to tend to these issues alternative illumination sources have been introduced, such as light emitting diodes (LEDs), for use in medical diagnostic instruments. LEDs generate considerably less heat, require less power, and also have increased working life as compared to halogen and incandescent bulb counterparts. Conversely, LEDs generate less light, which can create issues given the nature of some medical targets (e.g., the ear) and also have spectral issues in terms of their color temperature, the latter being a specific concern for various medical applications in which emission of white light is preferred. In some instances, instruments have been equipped with multiple LEDs disposed in a ring or other similar configuration in order to provide sufficient amounts of illumination to a medical target. In these latter instances, however, the light beam that is produced fails to produce a coherent and uniform spot.

BRIEF DESCRIPTION

According to one aspect, there is provided a medical diagnostic instrument comprising a housing having an interior, a distal end and an opposing proximal end. A supporting member disposed within the interior of the housing supports a plurality of LEDs. A light guide made from a light transmissive material is distally disposed in relation to the LED supporting member for transmitting light emitted by the plurality of LEDs through the distal end of the housing. According to at least one version, the light guide is tapered and can be provided with a patterned surface along either the distal and/or the proximal end. The patterned surface is configured so as to uniformly distribute or merge the light emitted from the plurality of LEDs into a homogenous annular spot onto an intended target.

According to another aspect, there is provided an otological instrument comprising a housing having a conical insertion portion on which a speculum tip is configured for attachment. A light guide within the housing is positioned in relation to the conical insertion portion. The light guide is made from a light transmissive material and defined by a distal end, as well as an opposing proximal end in which at least one LED is adjacently disposed.

In one version, at least one of the distal or proximal end of the light guide is provided with a facing or end surface having a pattern disposed thereon. For example, the distal end of the light guide can be provided with a suitably patterned surface. According to another embodiment, the proximal end of the light guide can be provided with a patterned surface with the remaining distal end being polished or suitably treated. When more than one LED is used as an illumination source, the patterned surface acts to more uniformly distribute the emitted light into a coherent and homogenous spot onto a target of interest (i.e., the tympanic membrane) and over a range of effective working distances.

According to another version, a plurality of LEDs can be provided proximate the proximal end of the light guide. In one version, the LEDs can be directly attached to the proximal end of the light guide and disposed in a spaced and circumferential configuration. One or more of the LEDs can be provided at various circumferential positions on the distal surface of the light guide. In one version, a plurality of discrete LEDs that each emit light of a different color is provided in an overlapping or staggered mounting sequence. According to one version, amber, green and blue LEDs can be used in combination to provide a spectral white light.

According to yet another version, a ring-like element can be provided proximate the rear or proximal surface of the light guide. In this version, the light guide can be defined by a substantially conical configuration having a distal end and an opposing proximal end in which a plurality of LEDs can be disposed (attached) to the ring in a spaced circumferential configuration. In one embodiment, a separate structural component can be intermediately disposed between the LED supporting element and the proximal end of the light guide. A set of apertures or pinholes can be provided in the intermediately disposed element between the LED ring and the proximal end of the light guide so as to create a collimated light beam. According to one version, the light guide can include a beveled or angled surface at its distal end.

One advantage provided by the herein described system is that of improved illumination relative to a medical target of interest enabling LEDs to be effectively used in a medical examination device, such as an otoscope, in order to provide a more uniform and consistent light source. Use of a suitably patterned surface enables the output of a plurality of LEDs to produce a coherent, uniform and homogenous illumination spot.

Another advantage provided is that the LEDs can be arranged or otherwise configured such that white light can be produced. Other spectral effects can further be realized, as well as elimination or minimization of stray light.

Yet another advantage is that the use of multiple LEDs will enable the illumination assembly to continue to function in spite of the loss of a single LED. On the other hand, prior illumination systems employing a single light source and a fiber optic bundle would be rendered inoperative.

These and other features and advantages will be readily apparent from the following Detailed Description, which should be read in conjunction with the accompanying drawings.

DETAILED DESCRIPTION

The following description relates to several varied embodiments of an LED-based illumination system for use in a specific medical diagnostic instrument (i.e., otoscope). It will be readily understood, however, that the concepts discussed herein are also applicable to other medical diagnostic instruments which can be suitably configured for viewing various medical targets.

The accompanying drawings are intended to provide a suitable frame of reference for the reader and for illustratively detailing the salient features of the herein-described LED-based illumination system in accordance with the several embodiments. However, these drawings are not necessarily drawn to scale and therefore should not be overly relied upon by the reader for purposes of sizing and the like.

Figure 1:
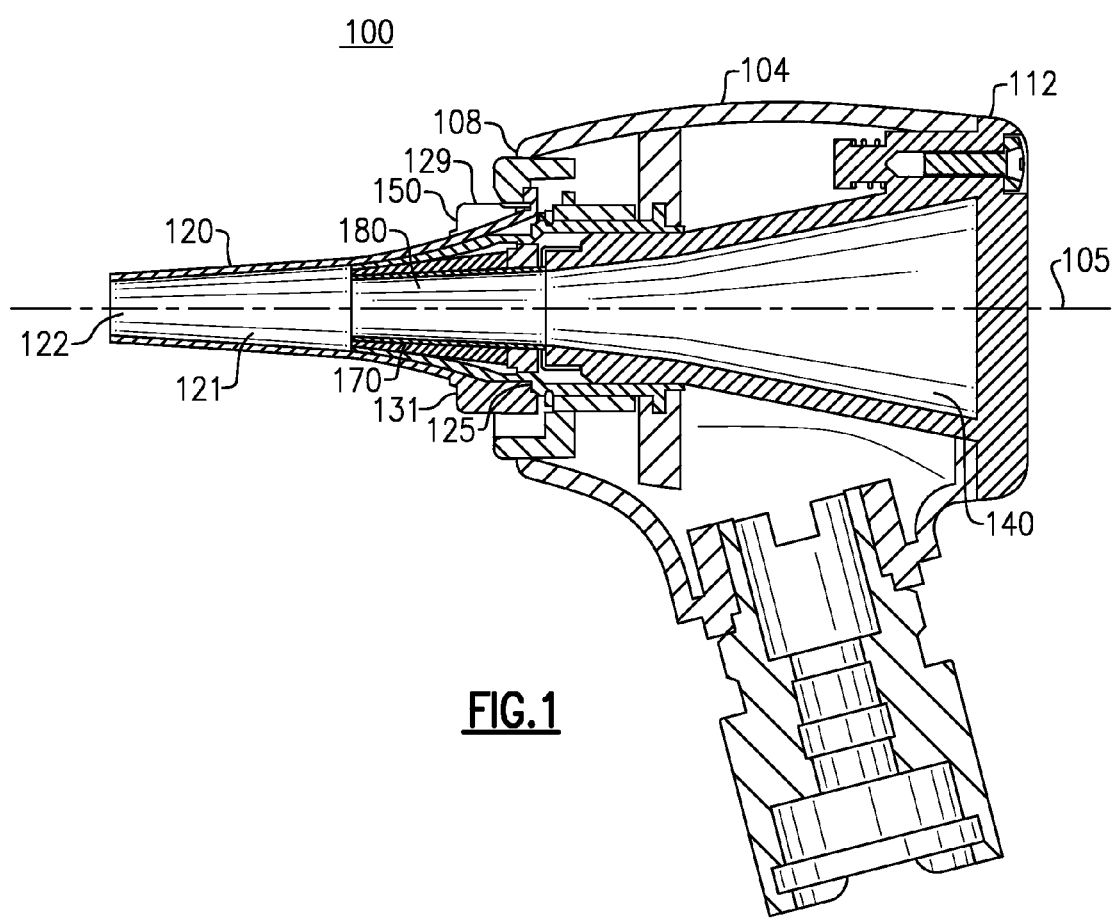
FIG. 1 is a side elevational view, taken in section, of a medical diagnostic instrument made in accordance with an embodiment.
Figure 2A:
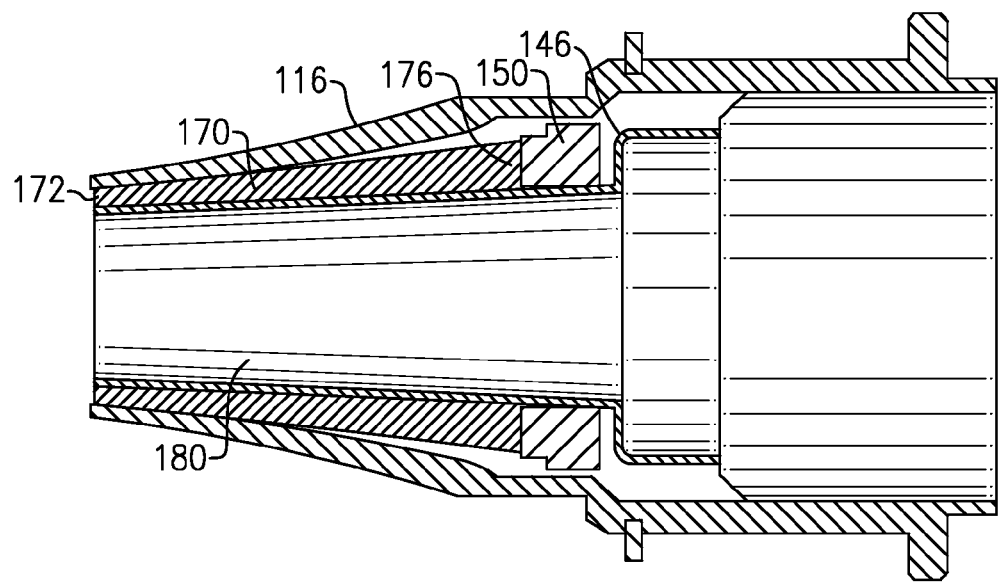
FIGS. 2(a) and 2(b) are partial side elevational views, taken in section, of the medical diagnostic instrument of FIG. 1.
Figure 2B:
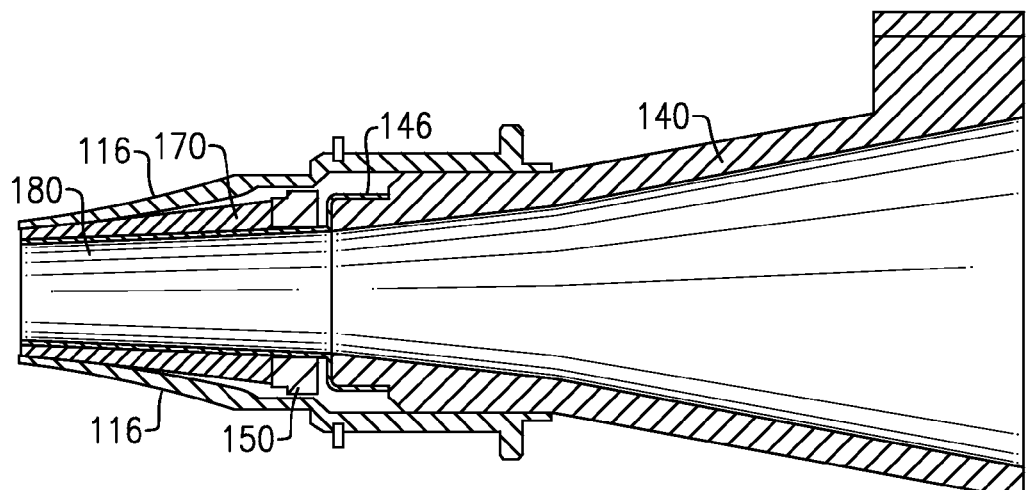

Turning to FIGS. 1-2(b), there is provided a medical diagnostic instrument 100 (i.e., an otoscope) having a housing 104 with defined and opposing distal and proximal ends 108, 112, respectively. An insertion portion 116 formed at the distal end 108 of the housing 104 is defined by a truncated frusto-conical shape that projects outwardly from the housing 104 and is configured to releasably receive a disposable speculum tip element 120 onto an exterior surface of the insertion portion 116. The speculum tip element 120 is similarly defined by a truncated frusto-conical shape that when fitted onto the distal insertion portion 116, extends distally (outwardly) therefrom, as shown. The speculum tip element 120 is defined by a hollow interior 121 as well as a distal tip opening 122 defined by a first diameter and an opposing proximal tip opening 125 defined by a second diameter that is significantly larger than the first diameter. According to this version, the proximal end of the speculum tip element 120 can include a series of engagement features (not shown) that are aligned with an attachment mechanism 129 of the instrument 100, including a rotatable knob 131 having a series of spaced arcuate slots (not shown) that permits the speculum tip element 120 to be selectively secured and/or removed/released from the instrument 100. When attached to the instrument 100, the speculum tip element 120 is designed to be inserted only to a predetermined distance within the outer ear of the patient (not shown) when an examination is performed by a caregiver. Specific features of an exemplary speculum tip element 120, including details involving the releasable mounting of the speculum tip element 120 to the instrument 100, are described in U.S. Pat. Nos. 7,354,275, 7,399,275, and 8,066, 634, the contents of each being incorporated by reference in their entirety.

Still referring to FIG. 1, FIG. 2(a) and FIG. 2(b), a plurality of other components are disposed within the hollow interior of the instrument housing 104, including an inner former 140 that extends rearwardly from the distal insertion portion 116 to provide structure for supporting other components within the housing interior. An LED supporting member 150 is positioned adjacent the proximal end of a conically shaped light guide 170 disposed within the interior of the distal insertion portion 116 of the herein described instrument 100. A distal portion 146 of the inner former 140 forms a shield 146 that surrounds the interior of the LED supporting member 150 and the light guide 170 with a formed portion of the shield engaging a read surface of the LED supporting member 150. The LED supporting member according to this embodiment is formed as a ring-like element made from an electrically insulating material such as plastic that includes a formed center through opening 154. The shield 146 can be integrally formed with the inner former 140 or alternatively can be provided as a separate component. The shield 146 can be made from any suitable material that will not permit light to pass therethrough. According to at least one embodiment, the shield can be made from a material such as blackened brass, in which the portion of the shield 146 proximal to (i.e., behind) the LED supporting element is epoxied thereto, wherein the shield can additionally function as a heat sink, dissipating the heat developed by the supported LEDs.

Figure 3:
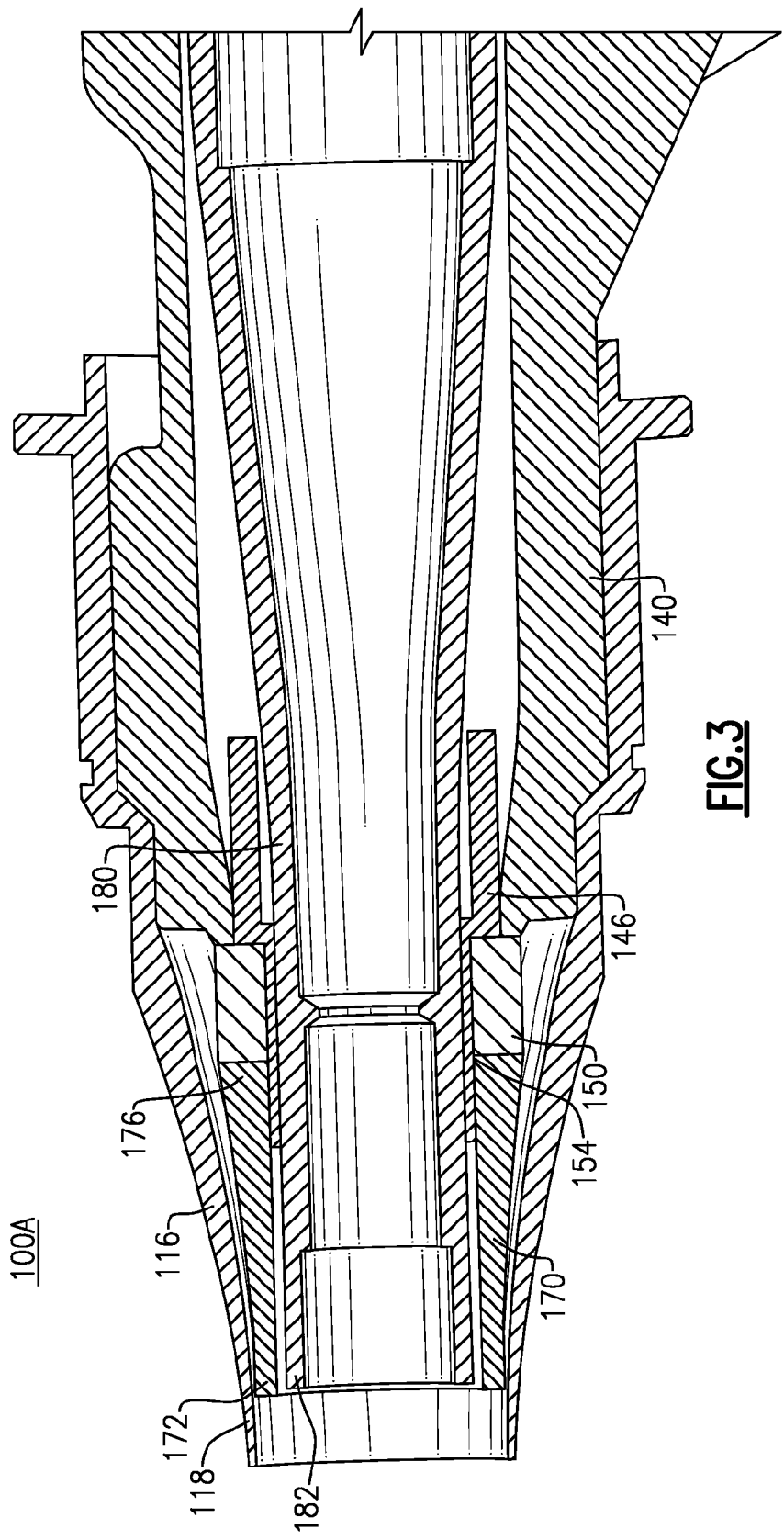
FIG. 3 is a sectioned view of the medical diagnostic instrument of FIGS. 1-2(b)

An alternative embodiment is shown in FIG. 3, including each of the above-noted components that are herein labeled with the same reference numbers for the sake of clarity. In addition to each of the above noted components, an optical tube 180 is further disposed within the hollow interior of the housing (the latter not shown in this view for clarity). The optical tube 180 extends through each of the inner former 140, the LED supporting member 150 and light guide 170 according to this embodiment with the distal end 182 of the optical tube 180 being disposed adjacent to, but within the distal end 118 of the distal insertion portion 116. The optical tube 180 is configured with at least one lens element (not shown) aligned along a suitable viewing axis 105, FIG. 1, extending through the respective openings of the light guide 150, optical tube 180, distal insertion portion 116 and the speculum tip element 120, FIG. 1.

Figure 4A:
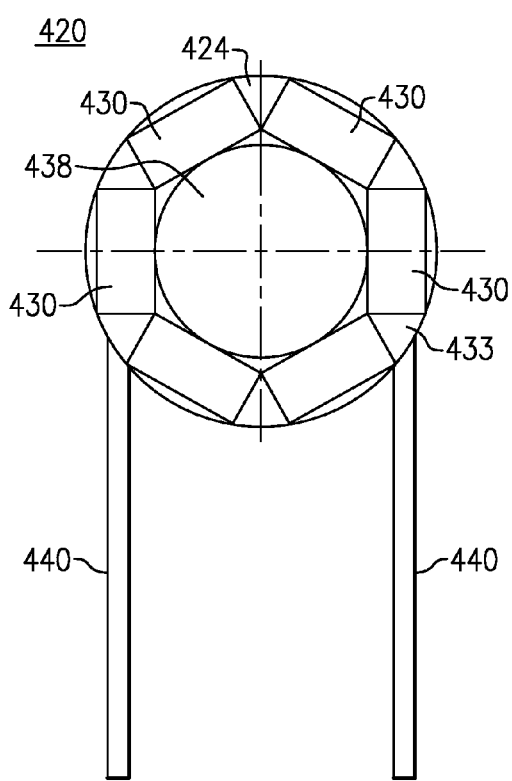
FIG. 4(a) is an end view of an LED ring in accordance with an embodiment.
Figure 4B:
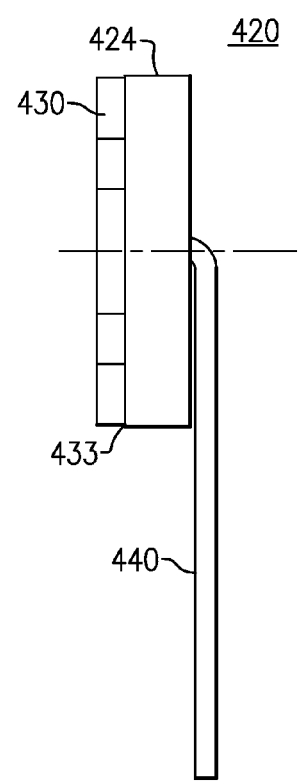
FIG. 4(b) is a side view of the LED ring of FIG. 4(a)

Referring to FIGS. 4(a) and 4(b), an exemplary LED supporting member 420 is depicted. According to this version, a total of six (6) LEDs 430 are disposed in spaced relation on a facing (distal) surface 433 of the LED supporting member 420, which is defined herein by a substantially ring-shaped element. The specific number of supported LEDs 430 can be easily varied depending, however, for example and depending on the intended target and/or amount of illumination needed in order to adequately view the intended target. For example, a typical LED that can be used for this purpose is an Osram GW JCLMS1.EC-GTHP-5L7N-L1N2 More specifically and according to this exemplary embodiment, each of the LEDs 430 are mounted in a circumferential fashion along an outer periphery of the LED supporting member 420 relative to a defined center through opening 438 on a single or multiple circuit boards. Alternatively, a configuration could interconnect the LEDs without a circuit board. For example, a ring could be cast with epoxy and the plurality of LEDs in a Teflon or other suitable mold using a plurality of connecting wires in order to link the supported LEDs. When attached, the center opening 438 of the LED supporting element 420 is preferably aligned with the optical axis of the instrument, such as viewing axis 105, FIG. 1. For purposes of mounting the LEDs 430, a series of cavities (not shown) can be provided such as by molding or forming, in the facing surface of the supporting member 420 for the fitting of same or by means of adhesives or other suitable mounting techniques to the circuit board(s). When assembled, a plurality of wire connectors 440 of the LEDs 430 extend outwardly from the LED supporting member 420 for connection to a contained power source, such as at least one battery (not shown) in which all of the supported LEDs 430 can be commonly and electrically coupled to one other. In at least one version, some or all of the LEDs 430 can be independently connected for selective operation.

Figure 5A:
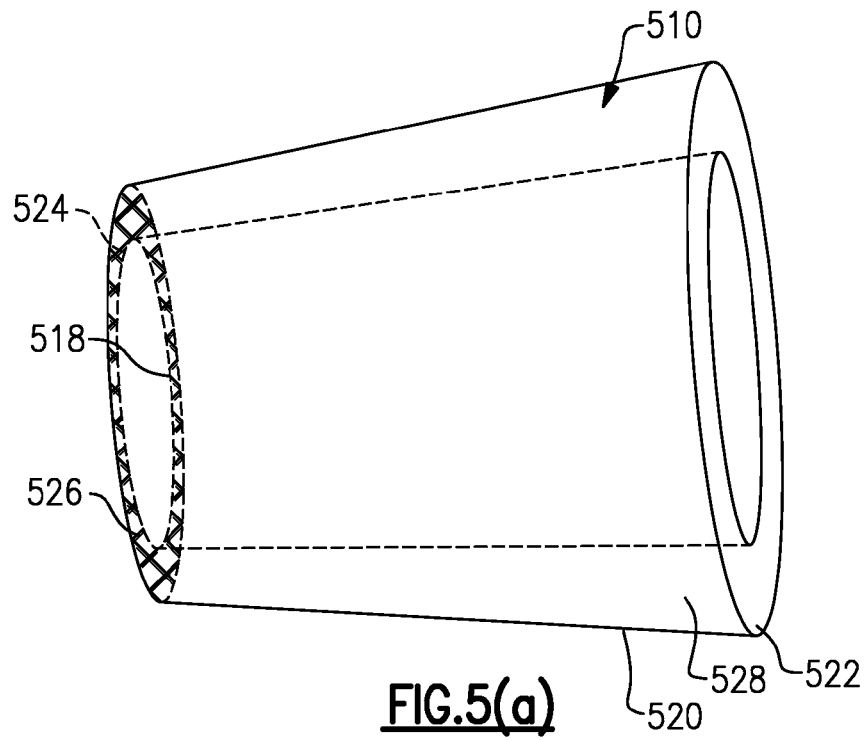
FIG. 5(a) is a side view of a light guide having a distributive patterned surface made in accordance with an embodiment.
Figure 5B:
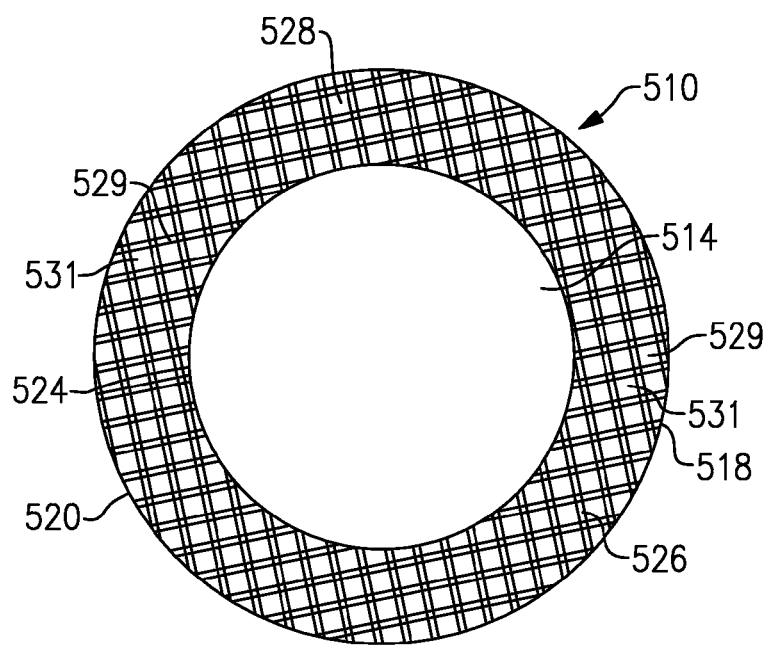
FIG. 5(b) is an end view of the light guide of FIG. 5(a)

A light guide 510 made in accordance with an exemplary embodiment is depicted in FIGS. 5(a) and 5(b), as represented by side elevational and a proximal end views, respectively. The light guide 510 can be made from a light transmissive material, such as acrylic or styrene. According to this specific embodiment, the light guide 510 is defined by a hollow conical cylindrical section that enables the light guide 510 to be positioned within the conically shaped distal insertion portion 116, FIG. 1. More specifically and according to this embodiment, the light guide 510 is defined as a hollow section that includes a distal end 518 having a first diameter and an opposing proximal end 522 having a second diameter that is substantially larger than the first diameter of the distal end 518. The light guide 510 is further defined by an exterior or outer surface 520 and a corresponding interior or inner surface 524 that combine to define an annular light transmissive portion 529. According to this version, a facing end surface of the proximal end 522 is preferably treated to provide a polished surface, while the distal end 518 of the light guide 510 is defined by a patterned end surface 526. The patterned end surface 526 can be created as part of the manufacturing process, such as by molding of same, or alternatively this surface 526 can be formed by embossing or other suitable techniques. According to this specific embodiment, the patterned end surface 526 of the light guide 510 is defined by a plurality of orthogonal line segments 529, 531 that are formed in an intersecting configuration and in which the line segments 529, 531 combine to form a grid-like array of rectangular areas that act to dissipate light as received by adjacently positioned LEDs (not shown in this view) of the LED supporting member, such as the LED supporting member 420, FIG. 4(a). More specifically, the grid-like array receives the emitted light from the LEDs via the polished proximal end 522 and light transmissive portion 529 of the light guide 510 and then uniformly distributes the light as a homogenous and substantially uniform ring of light toward the target of interest.

Figure 5C:
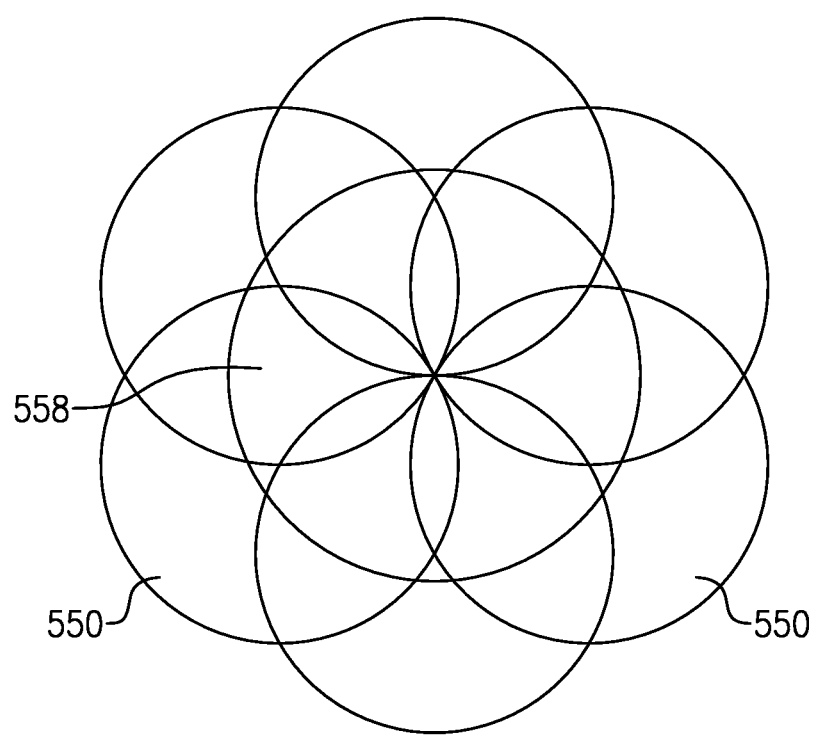
FIG. 5(c) depicts the effect of light from a plurality of emitted LEDs being directed at a target without a patterned surface such as depicted in FIGS. 5(a) and 5(b)

The patterned surface 526, FIG. 5(b), enables the output of a plurality of supported LEDs to be more uniformly directed at an intended target. Referring to FIG. 5(c), each individually supported LED of a ring of supported LEDs (not shown) would ordinarily emit a cone of light 550. In the absence of a patterned surface and following transmission through a light guide (not shown), a series of overlapping areas of light 558 are created. Providing a patterned surface 526, FIGS. 5(a) and 5(b), on at least one end of the light guide more evenly distributes the emitted light and produces a homogenous illumination spot that is much more consistent and uniform in terms of intensity and brightness.

Figure 6A:
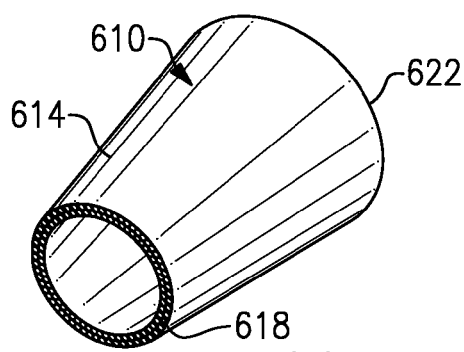
FIGS. 6(a)-6(e) are views of a light guide made in accordance with another embodiment.
Figure 6B:
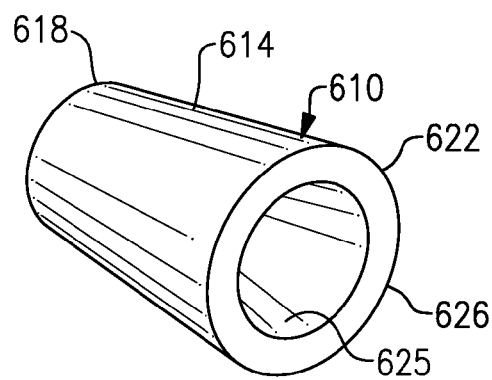
Figure 6C:
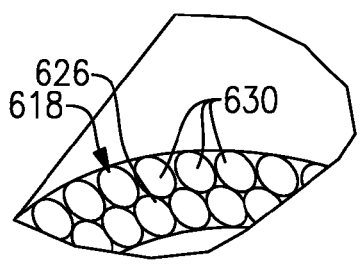
Figure 6D:
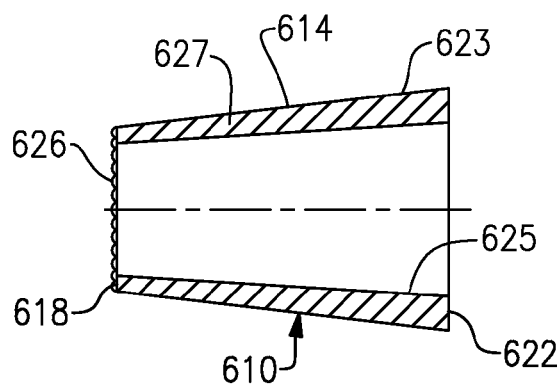
Figure 6E:
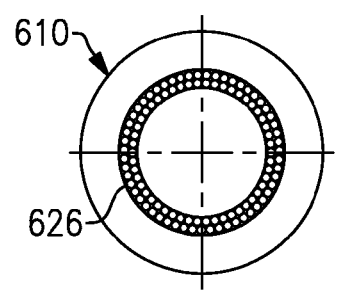

Another light guide 610 is depicted in FIGS. 6(a)-6(e) for use in the herein described LED-based illumination system. According to this embodiment, the light guide 610 is made from a light transmissive material. For example, the light guide 610 can be made from a moldable plastic, glasscore/clad molded in a similar configuration, fluid-filled light pipes, elastomeric material or the like. According to this version, the light guide 610 is further defined by a hollow conical body 614 having a distal end 618 defined by a first diameter and an opposing proximal end 622 defined by a second diameter that is substantially larger than the first diameter at the distal end 618. As in the preceding, the light guide 610 is further defined by an outer or exterior surface 623 as well as a corresponding inner or interior surface 625 that combine to define an overall thickness of the light guide that serves as an annular light transmissive portion 627. In this specific version and as best shown in FIGS. 6(c) and 6(e), the distal end 618 is provided with a patterned end surface 626 that is defined by a plurality of adjacent hemispherical protrusions 630 which are evenly and uniformly disposed in a circumferential and radially spaced configuration. According to this embodiment, two adjacent ringlets of protrusions 630 are provided, although it will be readily apparent that this parameter including the size, spacing and shape of the hemispherical protrusions or patterns employed can be easily varied depending on the application. According to this embodiment, the facing surface at the proximal end 622 can be polished. In use, the LED supporting member (not shown) is placed in proximity with the proximal end 622 and emitted light is directed through the light transmissive portion 627 and through the patterned distal end surface 626 and the protrusions 630 that are evenly configured in order to effectively and uniformly disperse the emitted light of the LEDs toward the intended target as a coherent and homogenous spot that can be provided over a range of working distances.

Variations of the preceding design can be provided. For example, yet another exemplary light guide 710 for use in an LED-based illumination system is depicted in FIGS. 7(a)-7(d). As in the preceding versions, this light guide 710 is made from a light transmissive material and defined by a substantially cylindrical section 714 having a narrowed distal end 718 with a first diameter and an opposing proximal end 722 having a second diameter that is larger than that first diameter. In at least one version, the light guide can be formed from a moldable transparent plastic.

Figure 7A:
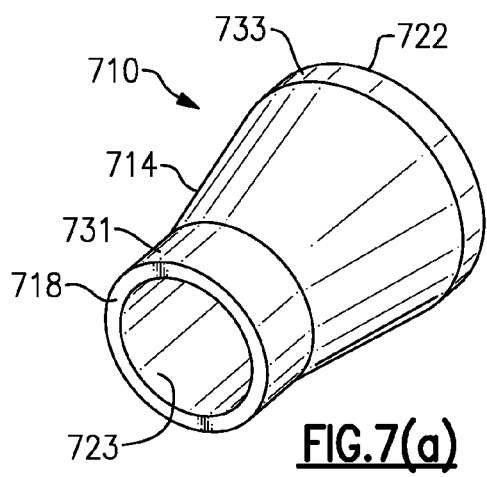
FIGS. 7(a)-7(d) are views of a light guide made in accordance with another embodiment.
Figure 7B:
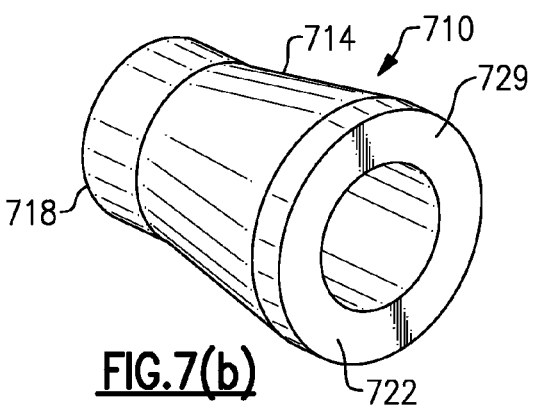
Figure 7C:
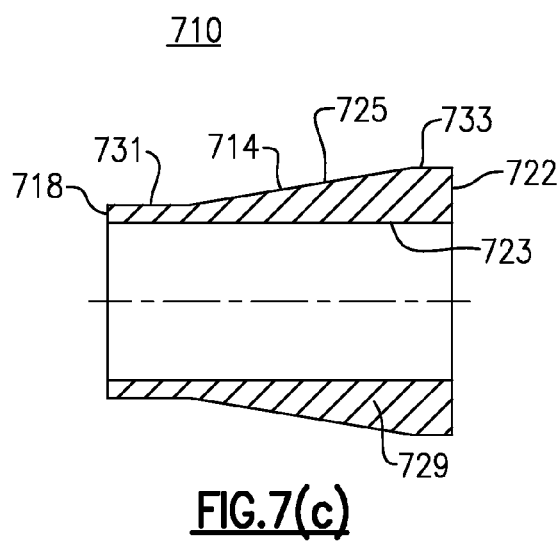
Figure 7D:
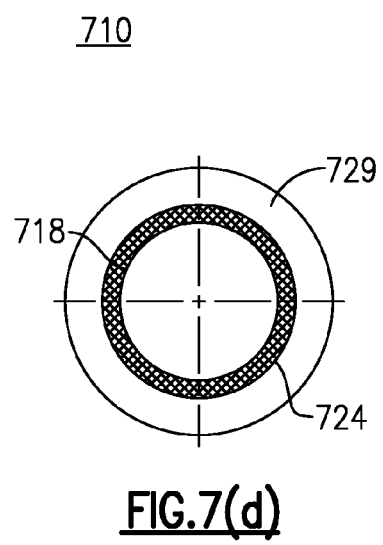

As in the preceding versions, the light guide is hollow. According to this specific embodiment, the thickness between an inner radial surface 723 and an outer or exterior radial surface 725 is at a maximum at the proximal end 722, with the thickness of the light guide 710 narrowing or tapering at the distal end 718, thereby defining an annular light transmissive portion 729. According to this version, an axial portion 731 of the distal end 718 is defined by a substantially constant thickness with an axial portion of the proximal end 722 being similarly defined. As noted, the thickness of the light guide 710 defines the light transmissive portion 729. According to this specific version, an outer circular face of the distal end 718 is provided with a patterned end surface 724 while the outer circular face at the opposing proximal end 722 is polished. An exemplary patterned end surface 724 is shown in FIG. 7(d). As noted, the light guide 710 is used in combination with a plurality of LEDs that are formed in a circular (ring) arrangement on an LED supporting member (not shown in this view) in which the LEDs are adjacent the proximal end 722 of the light guide 710 and in which emitted light is directed through the light transmissive portion 729 of the light guide 710 to the distal end 718 and through the distal opening of the distal insertion portion 116, FIG. 1, and the speculum tip element 120, FIG. 1. As in the preceding, the patterned end surface 724 enables the emitted light of the LEDs to be dispersed toward the intended target in which the light from the disparate LEDs are effectively and uniformly distributed as a coherent and homogenous spot and in which this spot can be produced over a range of working distances of the instrument.

Figure 8A:
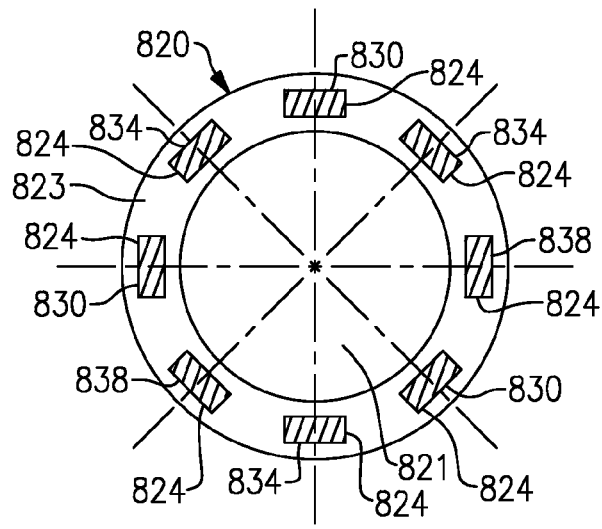
FIG. 8(a) is an end view of a supporting element including a plurality of LEDs disposed in accordance with a mounting configuration.
Figure 8B:
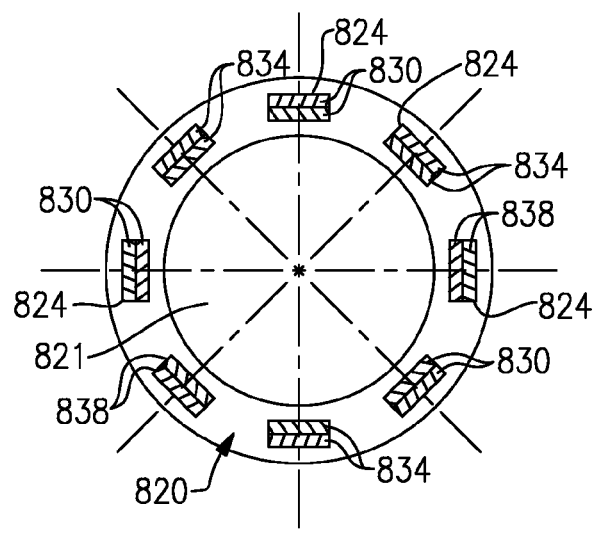
FIG. 8(b) is an end view of the supporting element of FIG. 8(a), including a plurality of LEDs disposed in accordance with another mounting configuration.
Figure 8C:
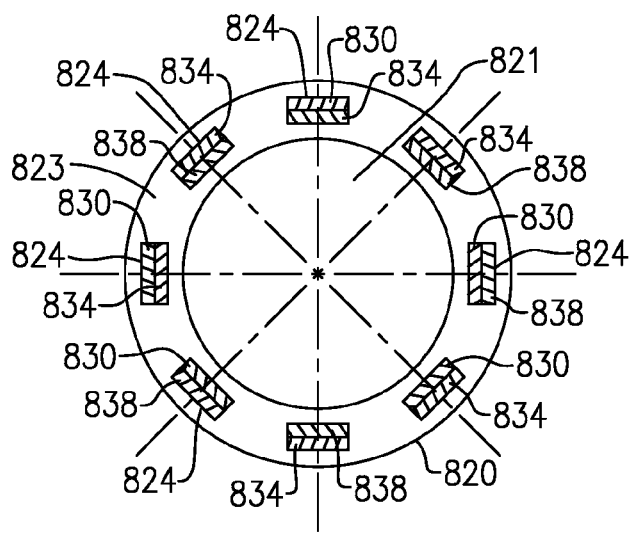
FIG. 8(c) is an end view of the supporting element of FIGS. 8(a) and 8(b), including a plurality of LEDs disposed in accordance with yet another mounting configuration.

Referring to FIGS. 8(a)-8(c), various versions of supported LEDs and LED supporting members are shown in various combinations for enabling a specific (e.g., white) light to be spectrally produced for the described illumination system. For purposes of describing these embodiments, similar parts are labeled with the same reference numerals for the sake of clarity. An LED supporting member 820 defined by a ring-like configuration supports a plurality of LEDs in a spaced circumferential manner about a defined center opening 821 for positioning and aligning same in relation to a light guide, such as those previously discussed in FIGS. 5(a)-7(d). The LEDs are attached either using adhesives or other suitable means in regard to a facing surface 823 of the supporting member 820 onto a single or independently mounted circuit boards. In a first version shown in FIG. 8(a), a plurality of LEDs are disposed in a spaced circumferential configuration provided on the facing surface 823 of the supporting member 820. A first LED 830 defined by a specific color (e.g., amber) is disposed in a first circumferential position 824 on the supporting ring element 820 with a second (e.g., green) LED 834 being disposed 45 degrees from the first LED 830 in a second circumferential position 824 of the supporting ring element 820. A third (e.g., blue) LED 838 is disposed in a position 90 degrees from the first LED 830 and 45 degrees from the second LED 834. The foregoing pattern is subsequently repeated, (i.e., amber, green, blue per arrow 844) about the outer circumference of the supporting ring element 820 with each LED 830, 834, 838 being equally spaced from an adjacent LED. A total of eight (8) LEDs are provided according to each of the specific embodiments that are described, but it will be readily apparent that the number and relative spacing of the supported LEDs can be varied depending, for example, the intended target of interest as well as the amount of illumination required to properly view the target of interest.

Referring to FIG. 8(b), there is provided an alternative configuration of plural LEDs as positioned at each of the spaced circumferential positions 824 of the supporting ring 820. More specifically and according to this version, a pair of amber LEDs 830 are disposed at the first circumferential position 824 and positioned in side by side relation. A second pair of green LEDs 834 are disposed at the second circumferential position 824, also in side by side relation with a third pair of blue LEDs 838 being disposed, according to this example, at the third circumferential position 824. As in the preceding version, this pattern of side by side LEDs is repeated over the remaining five (5) circumferential positions 824, as depicted. It should be noted that though two LEDs are shown herein in side by side relation at each ring position, it will be readily understood that the number of LEDs provided at each circumferential position of the supporting element can easily be varied, for example, depending on the application required.

In a third variation, shown as FIG. 8(c), side by side LEDs are provided at the spaced circumferential positions 824 of the supporting element 820 in a staggered configuration. More specifically and according to this version, an amber LED 830 is disposed in side by side relation at the first circumferential position 824 with a green LED 834. At a second spaced position, a green LED 834 is disposed in side by side relation with a blue LED 838. At a third spaced position, a blue LED 838 is disposed in side by side relation with an amber LED 830. In this arrangement and at the first circumferential position, the amber LED 830 is disposed radially outward relative to the green LED 834. Likewise and in the second circumferential position 824, the green LED 834 is disposed radially outward relative to the blue LED 838 and in the third circumferential position, the blue LED 838 is disposed radially outward relative to the amber LED 830. As in the preceding, this mounting pattern is repeated for the remaining five (5) circumferential positions 824 on the LED supporting ring element 820. A noted, however, the overall number of positions and spacing of the LED mounting positions can be suitably varied.

In each of the foregoing embodiments and upon activation, there is a level of color mixing in which the adjacent color LEDs 830, 834, 838 spectrally combine to form a substantially white light.

Figure 9:
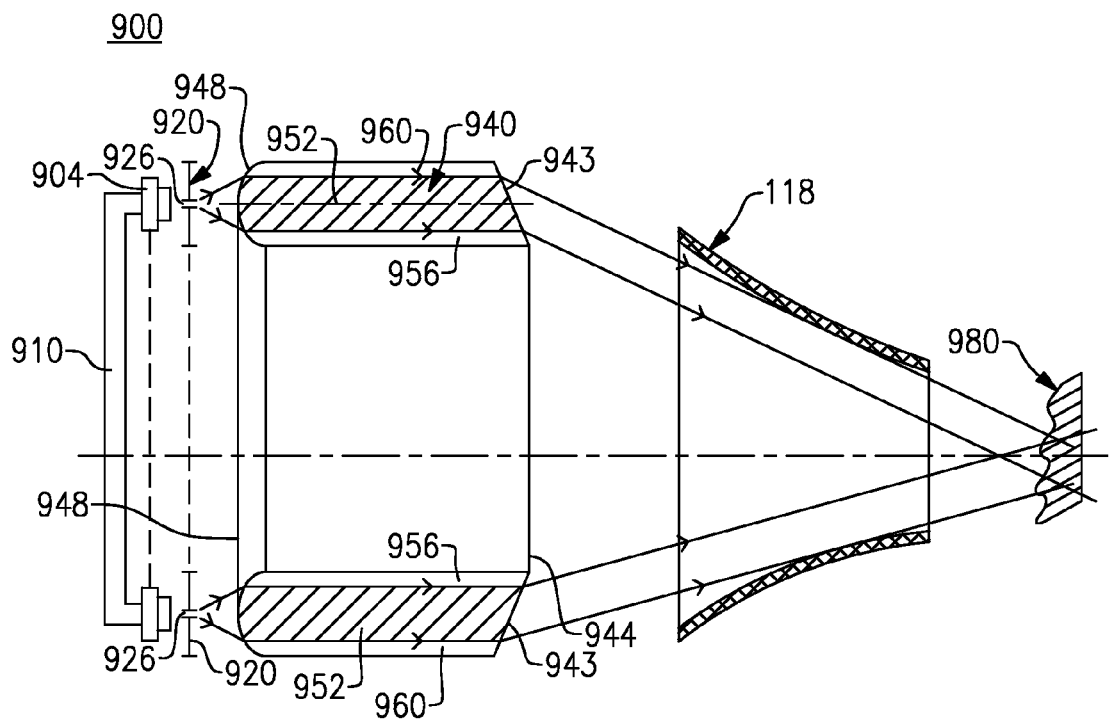
FIG. 9 is a side elevational view of an illumination system including an intermediate mask element positioned between a supported source of LEDs and a light guide.
Figure 10:
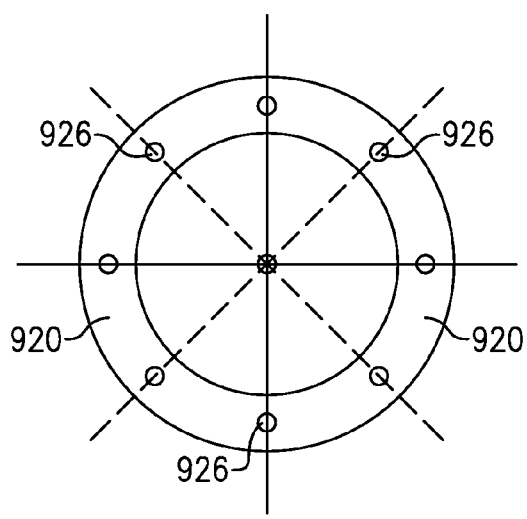
FIG. 10 is an end view of the intermediate mask element of FIG. 9.

Referring to FIGS. 9 and 10, there is depicted an illumination system 900 made in accordance with another exemplary embodiment for use in a medical diagnostic instrument such as an otoscope (partially shown only in FIG. 9). A plurality of LEDs 904 are supported in a ring-like configuration on a supporting member 910, such as previously described and fixedly mounted thereon. According to this specific embodiment, a total of eight (8) LEDs 904 are disposed in a spaced circumferential configuration about a center opening in the supporting member 910, although the overall number can be suitably varied depending on the application (medical target) and the amount of illumination necessary for illuminating same. A mask element 920 is disposed intermediately between the LED supporting member 910 and the proximal end 948 of an arranged light guide 940. According to this specific embodiment, the mask element 920 is defined by a substantially circular section made from a suitable material, such as a durable non-transparent plastic and including a plurality of pinholes 926 that are evenly spaced from one another in a circumferential arrangement at the outer periphery. As shown in FIG. 9, the pinholes 926 are commonly defined by a diameter that is less than the diameter of the light emitting portion of each adjacent LED 904.

Referring specifically to FIG. 9, the light guide 940 according to this exemplary embodiment is made from a section of a light transmissive material, such as acrylic or a plastic having a hollow interior. According to this specific version, the light guide 940 is defined by a distal end 944 and an opposing proximal end 948. Additionally, an annular pocket or tunnel 952 is formed between an inner radial surface 956 and an outer radial surface 960 of the light guide 940. The defined tunnel 952 axially extends between the distal and proximal ends 944, 948 of the light guide 940 and is configured to permit light transmission therethrough. According to this embodiment, the distal end 944 of the light guide 940 is defined by an angled or beveled surface 943 that extends inwardly toward the outer radial surface 960. In addition and though not shown, either or each end of the light guide can include a patterned surface, as previously discussed, that is configured to uniformly distribute the light from the multiple LEDs.

In operation, light that is emitted from the each of the LEDs 904 disposed and supported by the LED supporting element 910 is collimated through a corresponding pinhole 926 of the intermediately disposed mask element 920, each of the pinholes 920 being centrally aligned relative to the LEDs 904. Emitted light is caused to pass into the distal end 944 of the light guide 940 as a collimated beam to be directed without internal reflection through the annular tunnel 952 and to the beveled surface 953 of the distal end 942. The latter angled surface 953 directs the transmitted light inwardly toward the speculum tip element 120, FIG. 1, as well as the intended target of interest (i.e., tympanic membrane, which is herein shown schematically as 980).

PARTS LIST FOR FIGS. 1-10

100 medical diagnostic instrument
104 housing
105 optical or viewing axis
108 distal end, housing
112 proximal end, housing
116 distal insertion portion
118 distal end, distal insertion portion
120 speculum tip element
121 hollow interior, speculum
122 distal tip opening, speculum
125 proximal tip opening, speculum
129 attachment mechanism
131 rotatable knob
140 inner former
146 portion, shield
150 LED supporting member
154 center through opening
170 light guide
172 distal end, light guide
176 proximal end, light guide
180 optical tube
182 distal end, optic tube
420 LED supporting member
430 LEDs
433 facing surface
438 center opening
440 wire connectors
510 light guide
514 hollow interior
518 distal end
520 outer (exterior) surface
522 proximal end
524 inner (interior) surface
526 patterned end surface
528 light transmissive portion
529 line segment
531 line segment
550 light output
558 overlapping areas
610 light guide
614 body, hollow conical
618 distal end, narrowed
622 proximal end, light guide
623 outer surface
625 inner surface
626 patterned end surface
627 light transmissive portion
630 protrusions
710 light guide
714 cylindrical section or body, light guide
718 distal end
722 proximal end
723 inner radial surface
724 patterned end surface
725 outer surface
729 light transmissive portion
731 axial portion
733 axial portion
820 supporting member, LED
821 center opening
823 facing surface
824 circumferential mounting positions
830 first (amber) LED
834 second (green) LEI
838 third (blue) LED
900 illumination system
904 LEDs
910 supporting element
920 mask element
926 pinholes
940 light guide
943 angled or beveled surface
944 distal end
948 proximal end
952 annular pocket or tunnel
956 inner radial surface
960 outer radial surface
980 tympanic membrane It will be readily apparent that other modifications and variations can be contemplated and within the intended ambits of this invention, and as claimed.

The invention claimed is:

1. A medical diagnostic instrument comprising:
a housing having an interior, a distal end and an opposing proximal end;
a supporting member disposed within the interior of the housing, the supporting member supporting a plurality of LEDs; and
a light guide made from a light transmissive material and having a distal end surface, an opposing proximal end surface and a hollow interior, the light guide being distally disposed in relation to the LED supporting member for transmitting light emitted by the plurality of LEDs through the distal end of the housing to a target, the supporting member being placed in contact with the proximal end surface of the light guide and in which at least one of the distal end surface or proximal end surface is formed as a patterned surface to substantially distribute emitted light from the plurality of LEDs into a single coherent and homogenous spot.

2. The diagnostic instrument according to claim 1, in which the LEDs are disposed on a facing end surface of the supporting member in a circumferential configuration.

3. The diagnostic instrument according to claim 2, including a plurality of circumferential locations on the facing end surface of the supporting member, and in which adjacently mounted LEDs are defined by the same color.

4. The diagnostic instrument according to claim 2, including a plurality of circumferential locations on the facing end surface of the supporting member, and in which adjacently mounted LEDs are defined by different colors.

5. The diagnostic instrument according to claim 1, in which more than one LED is disposed in a spaced circumferential location on the supporting member.

6. The diagnostic instrument according to claim 5, in which at least two LEDs are disposed in side by side relation in each circumferential location on the supporting member.

7. The diagnostic instrument according to claim 6, in which the at least two LEDs in side by side relation in the same circumferential location emit a light of the same color.

8. The diagnostic instrument according to claim 6, in which the at least two LEDs in side by side relation in the same circumferential location are not the same color.

9. The diagnostic instrument according to claim 1, including a mask element disposed between the light guide and the supporting member, the mask element having a plurality of apertures, each of the apertures creating pinholes to enable collimation of emitted light from an adjacently aligned LED.

10. The diagnostic instrument according to claim 1, wherein the patterned surface includes a series of intersecting line segments formed into the at least one end surface of the light guide.

11. The diagnostic instrument according to claim 1, wherein the patterned surface is defined by a plurality of hemispherical protrusions formed into the at least one end surface of the light guide.

12. The diagnostic instrument according to claim 1, wherein the thickness of the light guide varies between the distal end and the proximal end.

13. The diagnostic instrument according to claim 1, wherein the thickness of the light guide is substantially constant over at least an axial portion.

14. An otological instrument comprising:
a housing having a conical insertion portion on which a speculum tip is configured for attachment;
a light guide positioned in relation to the conical insertion portion, the light guide being made from a light transmissive material and defined by a distal end surface, as well as an opposing proximal end surface in which at least two LEDs are adjacently disposed and in which the light guide includes a patterned surface formed into at least one of the distal and proximal end surfaces, the patterned surface being configured to substantially distribute the light emitted by the at least two LEDs into a single coherent and homogenous spot.

15. The instrument according to claim 14, in which the formed patterned surface is defined by one of a grid-like array or a plurality of adjacent hemispherical projections.

16. The instrument according to claim 14, in which a plurality of said LEDs are mounted to a supporting member, the LEDs being mounted in a circular configuration on a facing surface of the supporting member arranged relative to the light guide.

17. The instrument according to claim 14, in which the light guide is hollow and has a thickness defining a light transmissive portion.

\* \* \* \* \*